US006393367B1

(12) United States Patent
Tang et al.

(10) Patent No.: US 6,393,367 B1
(45) Date of Patent: May 21, 2002

(54) METHOD FOR EVALUATING THE QUALITY OF COMPARISONS BETWEEN EXPERIMENTAL AND THEORETICAL MASS DATA

(75) Inventors: Chao Tang; Wenzhu Zhang; David Fenyö ; Brian T. Chait, all of New York, NY (US)

(73) Assignee: Proteometrics, LLC, New York, NY (US)

( * ) Notice: Subject to any disclaimer, the term of this patent is extended or adjusted under 35 U.S.C. 154(b) by 0 days.

(21) Appl. No.: 09/507,180

(22) Filed: Feb. 19, 2000

(51) Int. Cl.[7] .................................................. G01N 33/00

(52) U.S. Cl. ............................. 702/19; 702/20; 702/22; 702/30; 436/89; 436/94; 436/173; 503/334; 503/417

(58) Field of Search .............................. 702/19, 20, 22, 702/30; 436/89, 94, 173; 503/417, 334

(56) References Cited

U.S. PATENT DOCUMENTS 5,240,859 A * 8/1993 Aebersold .................... 436/161
5,538,837 A 7/1996 Yates, III et al.

OTHER PUBLICATIONS

Henzel W.J., Billeci T.M., Stultz J.T., Wong S. C., Grimley C., and Watanbe C., "Identifying Proteins from two–dimensional gels by Molecular Mass Searching of Peptide Fragments in Protein Sequence Databases," *Proc. Natl. Acad. Sci.* (*USA*) 1993, 90, 5011–5015.

Mann M., Hojrup P., and Roepstorff P., "Use of Mass Spectrometric Molecular Weight Information to Identify Proteins in Sequence Databases," Biol. Mass Spectrom. 1993, 22, 388–345.

Pappin D.J.C., Hojrup P., and Bleasby A.J., "Rapid Identification of Proteins by Peptide–Mass Fingerprinting," Current Biol. 1993, 3, 327–332.

Yates J.R., III, Speicher S., Griffin P.R., and Hunkapiller T., "Peptide Mass Maps: A Highly Informative Approach to Protein Identification," Anal. Biochem. 1993, 214, 397–408.

James P, Quadroni M, Carafoli E, Gonnet G., "Protein Identification by Mass Profile Fingerprinting," *Biochem. and Biophys. Res. Commun.* 1993, 195, 58–64.

Mortz E., Vorm O., Mann M., Roepstorff P., "Identification of Proteins in Polyacrylamide Gels by Mass Spectrometric Peptide Mapping Combined with Database Search," *Biol. Mass Spectrom.* 1994, 23, 249–261.

James P, Quadroni M, Carafoli E, Gonnet G., "Protein Identification in DNA databases by Peptide Mass Fingerprinting," *Protein Sci.* 1994, 3, 1347–1350.

(List continued on next page.)

*Primary Examiner*—Marc S. Hoff
*Assistant Examiner*—Hien Vo
(74) *Attorney, Agent, or Firm*—Hoffman & Baron, LLP; Irving N. Feit

(57) ABSTRACT

A method for determining the probability that a biological molecule identification is incorrect for a chosen significance level is provided. The method includes comparing experimental mass data of an unknown biological molecule with theoretical mass data and calculating a score for each comparison; selecting at least two scores from the scores to form a primary data set; generating artificial data sets from the primary data set; calculating a sample mean for each artificial data set; estimating population mean and population standard deviation from the sample means wherein the population is based on the distribution underlying the primary dataset; computing a Z score from the population mean and population standard deviation for each score to standardize the scores; choosing a significance level; and comparing a test Z score to a Z score of the chosen significance level to determine the probability that the biological molecule identification is incorrect.

40 Claims, 15 Drawing Sheets

OTHER PUBLICATIONS

Cottrell J.S., "Protein Identification by Peptide Mass Fingerprinting," *Peptide Research*. 1994, 3, 115–124.

Cordwell S.J., Wilkins M.R., Cerpa–Poljak A., Gooley A.A., Duncan M., Williams K.L., and Humprey–Smith I., "Cross–Species Identification of Proteins Separated by Two–Dimensional Gel Electrophoresis Using Matrix–Assisted Laser Desorption Ionisation/Time–Of–Flight Mass Spectrometry and Amino Acid Composition," *Electrophoresis*. 1995, 16, 438–443.

Jensen O.N., Podtelenikov A.V, Mann M., "Delayed Extraction Improves Specificity in Database Searches by Matrix–Assisted Laser Desorption/Ionization Peptide Maps," *Rap. Commun. Mass Spectrom*. 1996, 10, 1371–1378.

Jensen O.N., Vorm O., Mann M., "Sequence Patterns Produced by Imcomplete Enzymatic Digestion or One–Step Edman Degradation of Peptide Mixtures as Probes For Protein Database Searches," *Electrophoresis*. 1996, 17, 938–944.

Courchesne P.L., Luethy R., Patterson S.D., "Comparison of In–Gel and On–Member Digestion Methods at Low to Sub–pmol Level for Subsequent Peptide and Fragment–Ion Mass Analysis Using Matrix–Assisted Laser–Desorption/Ionization Mass Spectrometry," *Electrophoresis*. 1997, 18, 369–381.

Zhang W., Chait B.T., "Protein Identification by Database Searching: A Bayesian Algorithm," *Proceedings of the 43rd ASMS Conference on Mass Spectrometry and Allied Topics*, Atlanta, Georgia, 1995, 643.

Eng J.K., McCormack A.L., Yates J.R., "An Approach to Correlate Tandem Mass Spectral Data of Peptides with Amino Acid Sequence in a Protein Database," *Amer. Soc. Mass Spec*. 1994, 5, 976–989.

Mann M. and Wilm M., "Error–Tolerant Identification of Peptides in Sequence Databases by Peptide Sequence Tags," *Anal. Chem*. 1994, 66, 4390–4399.

Yates J.R., Eng J.K., McCormack A.L., Schieltz D., "Method to Correlate Tandem Mass Spectra of Modified Peptides to Amino Acid Sequences in the Protein Database," *Anal. Chem*. 1995, 67, 1426–1436.

Yates J.R., Eng J.K., McCormack A.L., "Mining Genomes: Correlating Tandem Mass Spectra of Modified and Unmodified Peptides to Sequences in Nucleotide Databases," *Anal. Chem*. 1995, 67, 3202–3210.

Griffin P.R., MacCoss M.J., Eng J.K., Blevins R.A., Aaronson J.S., Yates J.R., "Direct Database Searching with MALDI–PSD Spectra of Peptides," *Rap. Commun. Mass Spec*. 1995, 9, 1546–1549.

Patterson, S.C., Aebersold, R., "Mass Spectrometric Approaches for the Identification of Gel–Separated Proteins," *Electrophoresis*. 1995, 16, 1791–1814.

Mortz E., O'Connor P., Roepstorff P., Kelleher N.L., Wood T.D., McLafferty F.W., Mann M., "Sequence Tag Identification of Intact Proteins by Matching Tandem Mass Spectral Data Against Sequence Data Bases," *Proc. Nat. Acad. of Sci*. (USA) 1996, 93, 8264–8267.

Figeys D., Ducret A., Yates J.R., Aebersold R., "Protein Identification by Solid Phase Microextraction—Capillary Zone Electrophoresis—Microelectrospray—Tandem Mass Spectrometry," *Nature Biotechnology*. 1996, 14, 1579–1583.

McCormack A.L., Schieltz D.M., Goode B., Yang S., Barnes G., Drubin D., Yates J.R., III, "Direct Analysis and Identification of Proteins in Mixtures by LC/MS/MS and Database Searching at the Low–Femtomole Level," *Anal. Chem*. 1997, 69, 767–776.

Fenyö D., Qin J., Chait B.T., "Protein Identification Using Mass Spectrometric Information," *Electrophoresis*. 1998, 19, 998–1005.

Zhang W., Chait B.T., "ProFound—An Expert For Protein Identification," *Proceedings of the 46th ASMS Conference on Mass Spectrometry and Allied Topics*, Atlanta, Georgia, 1998, 969.

Yates J.R., "Database Searching Using Mass Spectrometry Data," *Electrophoresis*. 1998, 19, 893–900.

Fenyö D., Beavis R., "Network–Based Bioinformatics in Protein Mass Spectrometry," *Mass Spectrometry of Biological Materials*. 1998, 435–460.

Clauser K.R., Baker P., Burlingame A.L., "Role of Accurate Mass Measurement (±10 ppm) in Protein Identification Strategies Employing MS or MS/MS and Database Searching," *Anal. Chem*. 1999, 71, 2871–2882.

* cited by examiner

FIG. 1 BACKGROUND KNOWLEDGE ABOUT PROTEIN IDENTIFICATION USING MASS SPECTROMETRY METHOD
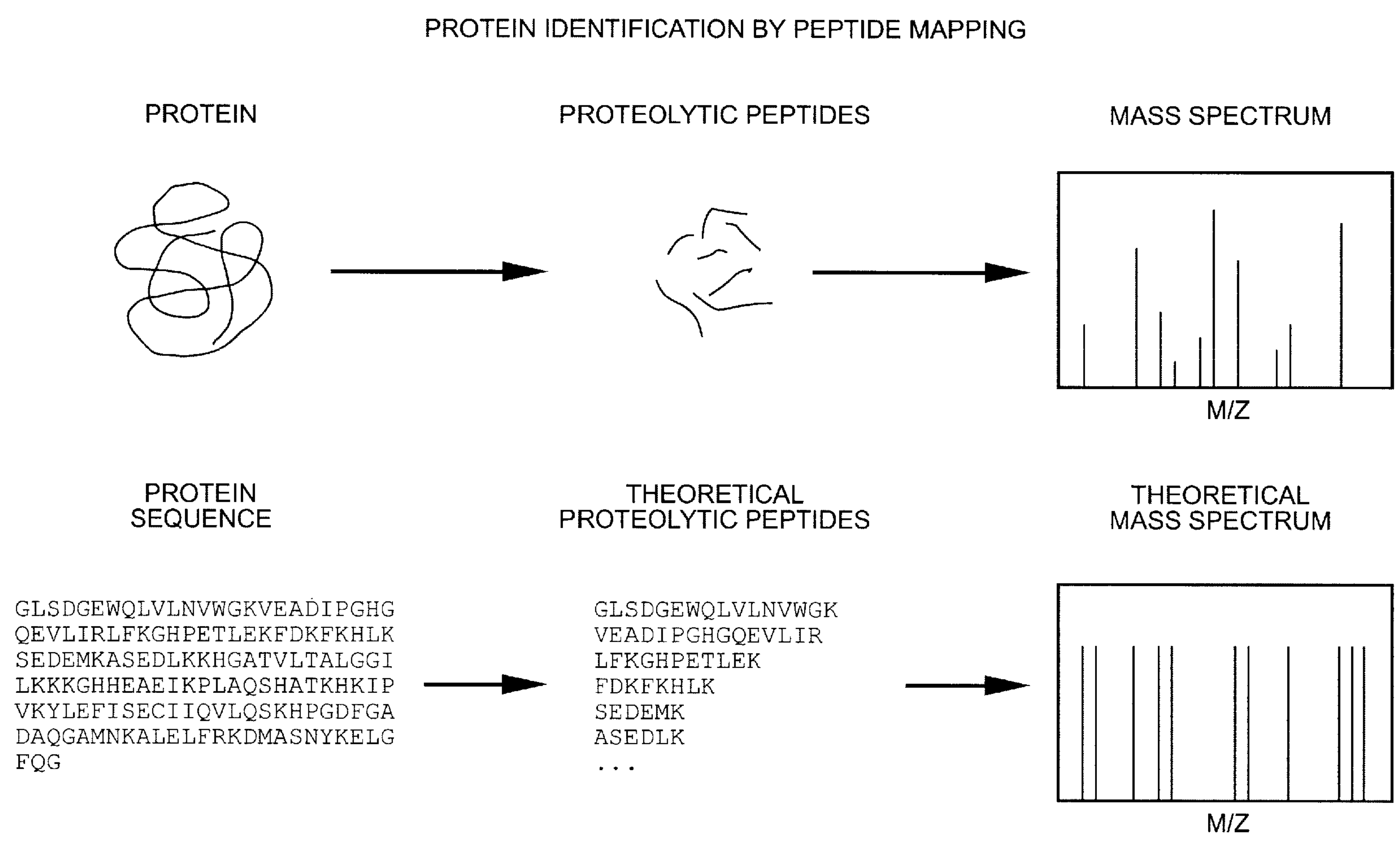

FIG. 2 A SAMPLE DATABASE SEARCH WHICH USES Z SCORE FOR RESULT EVALUATION

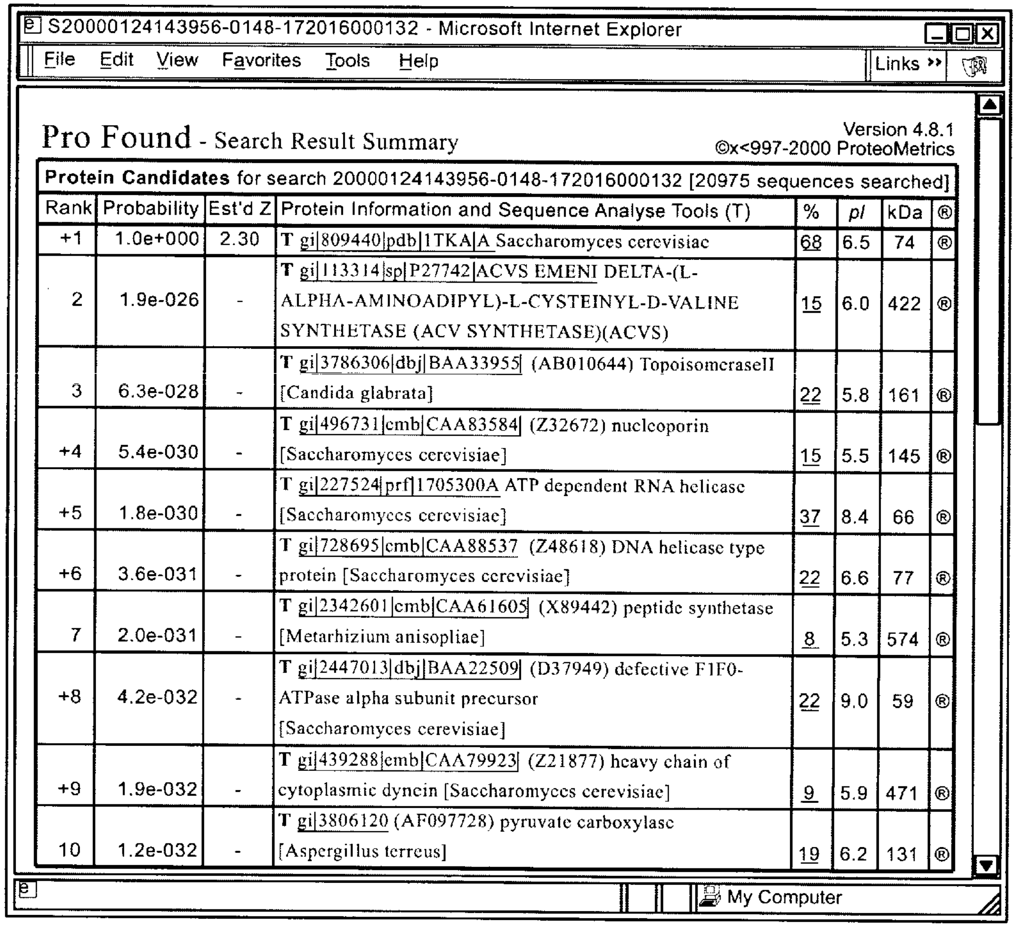
S20000124143956-0148-172016000132 - Microsoft Internet Explorer

File Edit View Favorites Tools Help Links »

Pro Found - Search Result Summary

Version 4.8.1
©x<997-2000 ProteoMetrics

Protein Candidates for search 20000124143956-0148-172016000132 [20975 sequences searched]

| Rank | Probability | Est'd Z | Protein Information and Sequence Analyse Tools (T) | % | pI | kDa | ® |
|---|---|---|---|---|---|---|---|
| +1 | 1.0e+000 | 2.30 | **T** gi\|809440\|pdb\|1TKA\|A Saccharomyces cerevisiae | 68 | 6.5 | 74 | ® |
| 2 | 1.9e-026 | - | **T** gi\|113314\|sp\|P27742\|ACVS EMENI DELTA-(L-ALPHA-AMINOADIPYL)-L-CYSTEINYL-D-VALINE SYNTHETASE (ACV SYNTHETASE)(ACVS) | 15 | 6.0 | 422 | ® |
| 3 | 6.3e-028 | - | **T** gi\|3786306\|dbj\|BAA33955\| (AB010644) TopoisomeraseII [Candida glabrata] | 22 | 5.8 | 161 | ® |
| +4 | 5.4e-030 | - | **T** gi\|496731\|emb\|CAA83584\| (Z32672) nucleoporin [Saccharomyces cerevisiae] | 15 | 5.5 | 145 | ® |
| +5 | 1.8e-030 | - | **T** gi\|227524\|prf\|1705300A ATP dependent RNA helicase [Saccharomyces cerevisiae] | 37 | 8.4 | 66 | ® |
| +6 | 3.6e-031 | - | **T** gi\|728695\|emb\|CAA88537 (Z48618) DNA helicase type protein [Saccharomyces cerevisiae] | 22 | 6.6 | 77 | ® |
| 7 | 2.0e-031 | - | **T** gi\|2342601\|emb\|CAA61605\| (X89442) peptide synthetase [Metarhizium anisopliae] | 8 | 5.3 | 574 | ® |
| +8 | 4.2e-032 | - | **T** gi\|2447013\|dbj\|BAA22509\| (D37949) defective F1F0-ATPase alpha subunit precursor [Saccharomyces cerevisiae] | 22 | 9.0 | 59 | ® |
| +9 | 1.9e-032 | - | **T** gi\|439288\|emb\|CAA79923\| (Z21877) heavy chain of cytoplasmic dynein [Saccharomyces cerevisiae] | 9 | 5.9 | 471 | ® |
| 10 | 1.2e-032 | - | **T** gi\|3806120 (AF097728) pyruvate carboxylase [Aspergillus terreus] | 19 | 6.2 | 131 | ® |

My Computer

FIG. 3 STEPS FOR RANDOM MATCH HYPOTHESIS TEST
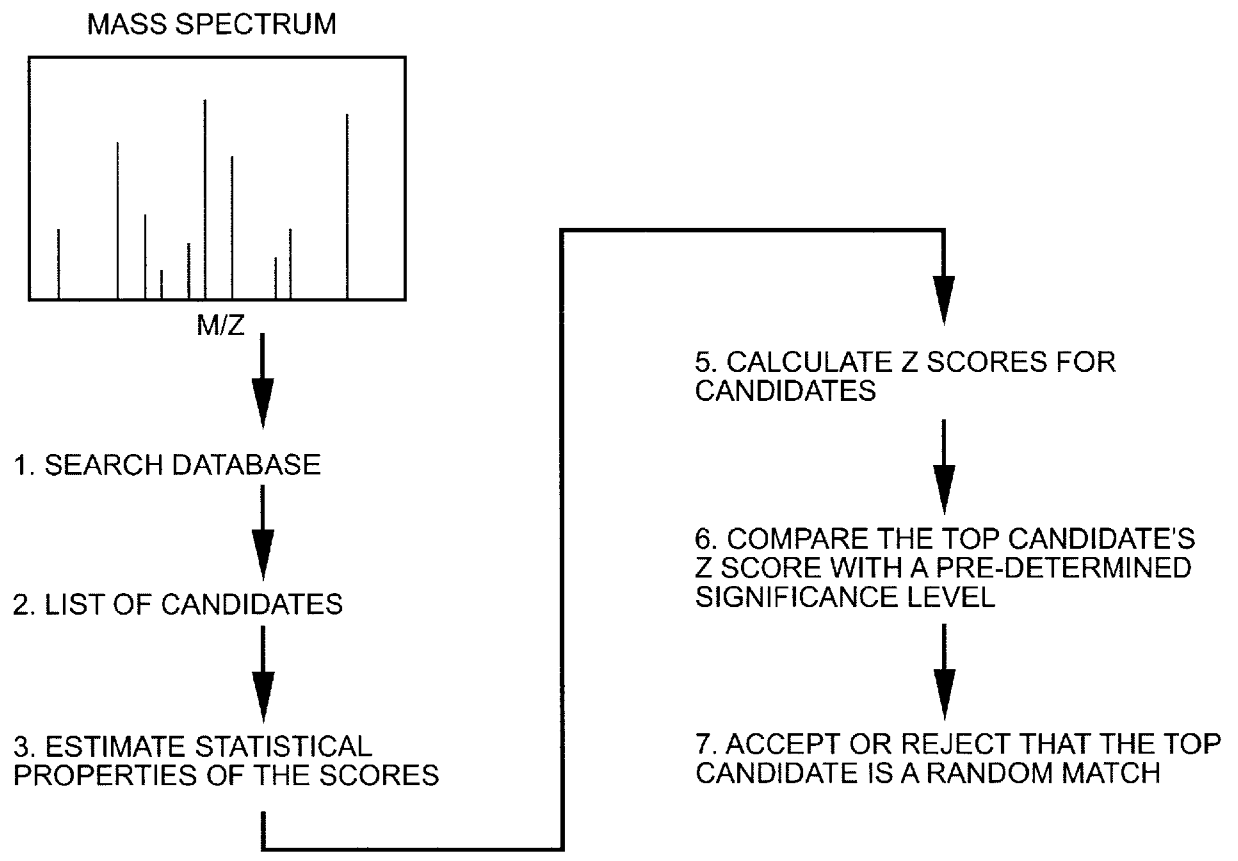

FIG. 4 A SAMPLE DATABASE SEARCH AND CANDIDATES' SCORE FREQUENCY DISTRIBUTION
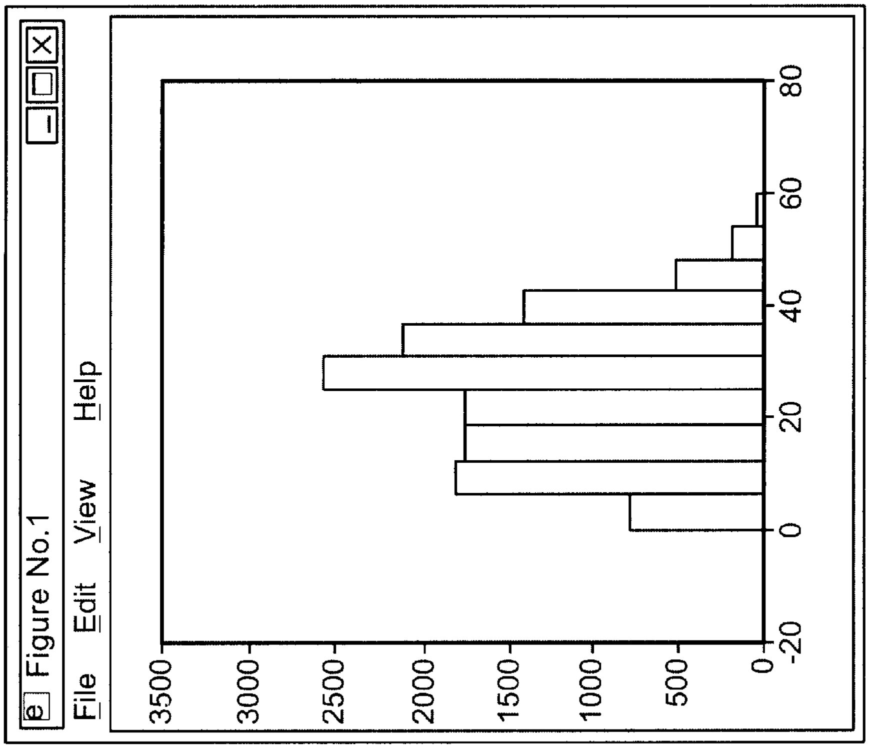

FIG. 5 ASSUMPTION: THE OVERALL DISTRIBUTION CONSISTS OF A NUMBER OF DISTRIBUTIONS
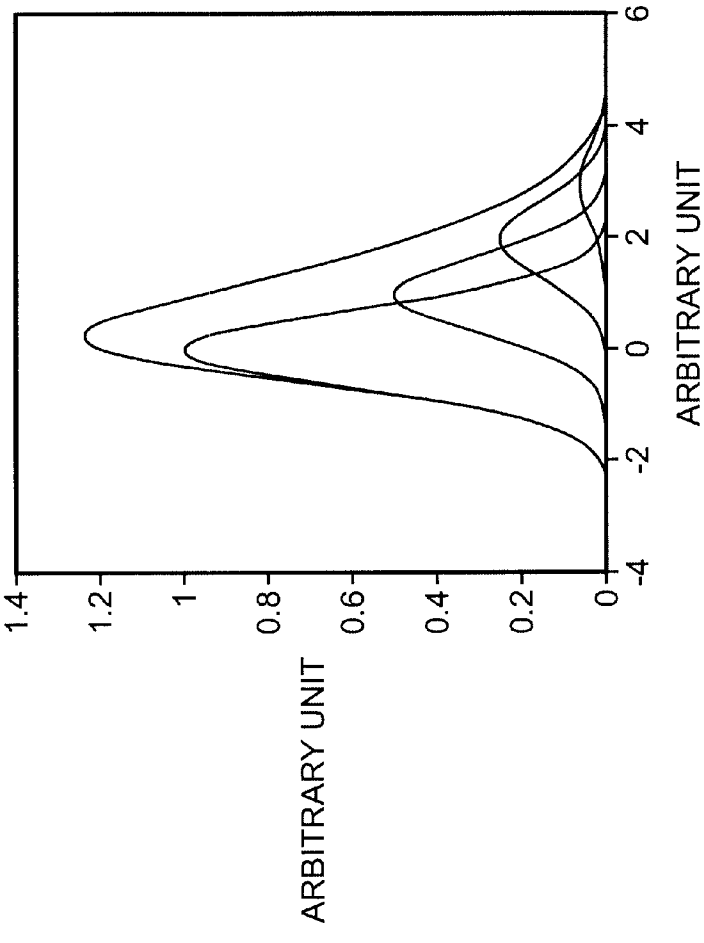

FIG. 6 A SAMPLE OF BOOTSTRAPPING EXPECTED DISTRIBUTION
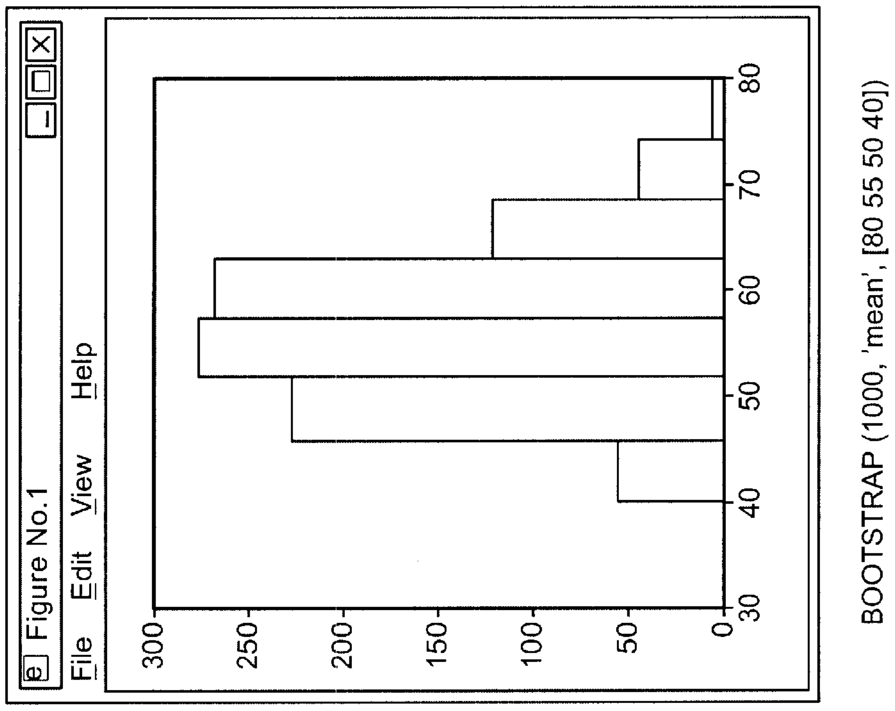

FIG. 7 NORMAL DISTRIBUTION AND Z SCORE
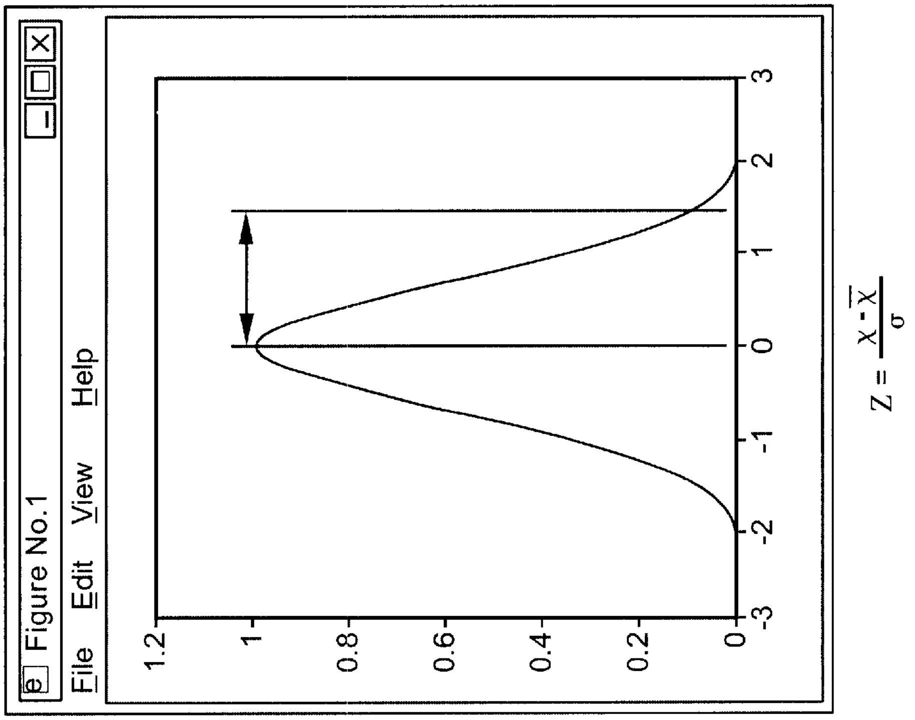

FIG. 8 THREE SIMULATIONS USING RANDOM SEQUENCES SHOWED GOOD AGREEMENT WITH ESTIMATED Z: THE INSTANCES HAVING GREATER THAN 1.65 WERE 2-4%. THE DISTRIBUTION OF NUMBER MASSES OF EACH SEQUENCE USED IN SIMULATION WERE SET TO MATCH THAT OF THE REAL WORLD DATA.
TOP Z SCORES FOR RANDOM SAMPLES FROM DIFFERENT DATABASE SEARCHES
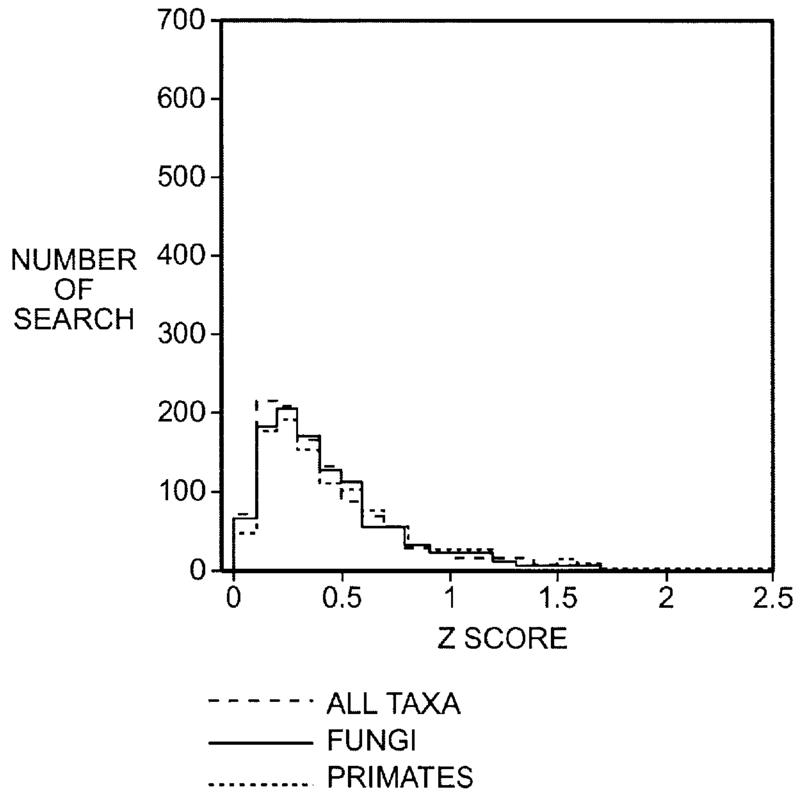

METHOD FOR EVALUATING THE QUALITY OF COMPARISONS BETWEEN EXPERIMENTAL AND THEORETICAL MASS DATA

BACKGROUND

An unknown biological molecule can be identified by comparing the mass data of the unknown biological molecule with mass data of known biological molecules.

For example, the rapid growth of available high quality DNA sequence data has made mass spectrometry (MS) combined with genome database searching a popular and potentially accurate method to identify proteins. Protein identification by mass spectrometry has proven to be a powerful tool to elucidate biological function and to find the composition of protein complexes and entire organelles.

In protein identification experiments, proteins are typically separated by gel electrophoresis, subjected to a protease having high digestion specificity (e.g. trypsin) and the resulting mixture of peptides is extracted from the gel and subjected to MS-analysis. The distribution of proteolytic peptide masses (peptide map) is compared with theoretical proteolytical peptide masses calculated for each protein stored in a protein/DNA sequence database.

There are various algorithms that attempt to identify the protein with the highest degree of similarity to the experimentally obtained peptide map. These algorithms yield the protein identified and an identification score. Due to imperfections in the protein separation and to incomplete extraction of the proteolytic peptides from the gel, the peptide map is typically incomplete with respect to the protein identified, and also contains a background of proteolytic peptide masses from one or several other proteins. Even if separation and extraction were perfect, posttranslational modifications of proteins would cause a proteolytic peptide mass distribution different from that predicted by the genome. Mass spectrometry determines a peptide mass mi to an accuracy $\pm\Delta m_i$, with $\Delta m_i/m_i$ typically >30 ppm. Within the mass range $m_i\pm\Delta m_i$ proteolytic peptide masses of several proteins in the genome can match. For these reasons, a database search using the information in a peptide map will not always identify a protein unambiguously.

Methods for evaluating the quality of a protein identification result have recently been provided. However, such methods may be computationally intensive, may not always be readily integrated with search programs and may need to set different standards for different databases. As increasingly complex biological problems are explored, simplified methods to evaluate the quality of a protein identification result are critical.

The object of the present invention is to provide a method for evaluating the quality of a biological molecule identification which is substantially less computationally intensive than prior methods. In one embodiment the present invention provides an evaluation of the quality of a protein identification score in a fraction of a second. Additionally, the present invention provides a criterion which indicates the quality of a particular protein identification result that will be the same level of significance regardless of the size of the database.

SUMMARY OF THE INVENTION

This and other objects, as will be apparent to those having ordinary skill in the art, have been met by providing a method for determining the probability that a biological molecule identification is incorrect for a chosen significance level and for a particular experimental condition, the method comprising: a)generating theoretical mass data for biological molecules; b) generating an experimental mass data for an unknown biological molecule; c) comparing the experimental mass data generated in step (b) with each theoretical mass data generated in step (a); d) calculating a score for each comparison in step (c), wherein the score is a function of the similarity between each of the data generated in step (a) and the data generated in step (b); e) selecting at least two scores from the scores in step (d) to form a primary data set, wherein the scores correspond to a comparison that denotes a degree of similarity between each of the data generated in step (a) and the data generated in step (b); f) generating a sufficient quantity of artificial data sets from the primary data set in step (e); g) calculating a sample mean for each artificial data set in step (f); h) estimating population mean and population standard deviation from the sample means generated in step (g); wherein the population is based on the distribution underlying the primary dataset; i) computing a Z score from the population mean and population standard deviation for each score calculated in step (d) to standardize the scores; j) choosing a significance level; and k) comparing a test Z score to a Z score of the chosen significance level to determine the probability that the biological molecule identification is incorrect. No particular order is required for the performance of these steps.

The invention further provides a computer usable medium for determining a probability that a biological molecule identification is incorrect for a chosen significance level and for a particular experimental condition, the computer usable medium comprising: a) a means for generating theoretical mass data for biological molecules; b) a means for generating experimental mass data for an unknown biological molecule; c) a means for comparing the experimental mass data generated in step (b) with each theoretical mass data generated in step (a); d) a means for calculating a score for each comparison in step (c), wherein the score is a function of the similarity between each of the data generated in step (a) and the data generated in step (b); e) a means for selecting at least two scores from the scores in step (d) to form a primary data set, wherein the scores correspond to a comparison that denotes a degree of similarity between each of the data generated in step (a) and the data generated in step (b); f) a means for generating a sufficient quantity of artificial data sets from the primary data set in step (e); g) a means for calculating a sample mean for each artificial data set in step (f); h) a means for using the sample means generated in step (g) to estimate population mean and population standard deviation; wherein the population is based on the distribution underlying the primary data set; i) a means for computing a Z score from the population mean and population standard deviation for each score calculated in step (d) to standardize the scores, j)a means for choosing a significance level; and k) a means for comparing a test Z score to the Z score of the chosen significance level to determine the probability that the identification is incorrect. No particular order is required for the performance of these steps.

The invention further provides a computer program product comprising: a computer usable medium having computer readable program code means embodied in said medium for determining a probability that a biological identification is incorrect for a chosen significance level and for a particular experimental condition, said computer program product including: computer readable program code means for causing a computer to generate theoretical mass data for known biological molecules, the biological molecules having been cleaved into constituent parts by a method that produces constituent parts; computer readable program code means for causing a computer to generate experimental mass data for an unknown biological molecule, the unknown biological molecule having been cleaved into constituent parts by a method that produces constituent parts; computer readable program code means for causing the computer to compare the mass data of the unknown biological molecule with mass data generated for the experimental condition for known biological molecules; computer readable program code means for causing the computer to calculate scores for each mass data comparison, wherein the scores are a function of similarity between mass data of the unknown biological molecule and mass data generated from the biological molecule database; computer readable program code means for causing the computer to select at least two scores from the calculated scores to form a primary data set, wherein the selected scores corresponds to a comparison which denotes a high degree of similarity; computer readable program code means for causing the computer to generate a sufficient quantity of artificial data sets from the primary data set; computer readable program code means for causing the computer to calculate a sample mean for each artificial data set; computer readable program code means for causing the computer to estimate population mean and standard deviation; wherein the population is based on the distribution underlying the primary data set; computer readable program code means for causing the computer to calculate a Z score from the population mean and population standard deviation for each score; computer readable program code means for causing the computer to choose a significance level; computer readable program code means for causing the computer to compare a test Z score to a Z score of the chosen significance level to determine the probability that the identification is incorrect. No particular order is required for the performance of these steps.

DESCRIPTION OF FIGURES

FIG. 1: Diagram demonstrating protein identification using mass spectrometry. The top mass spectrum, generated by an experimental protein, is compared with mass spectrum generated by theoretical proteins.

FIG. 2: A sample database search that uses Z score for result evaluation.

FIG. 3: Flow chart showing steps for random match hypothesis test.

FIG. 4: A score frequency distribution resulting from a sample database search.

FIG. 5: A graph of the assumption that the overall score frequency distribution consists of a number of smaller distributions.

FIG. 6: A graph of a sample of bootstrapping expected distribution

FIG. 7: A graph of a normal distribution and formula for Z score.

FIG. 8: A graph of top Z scores for random samples from different database searches.

DETAILED DESCRIPTION

Figure 10:
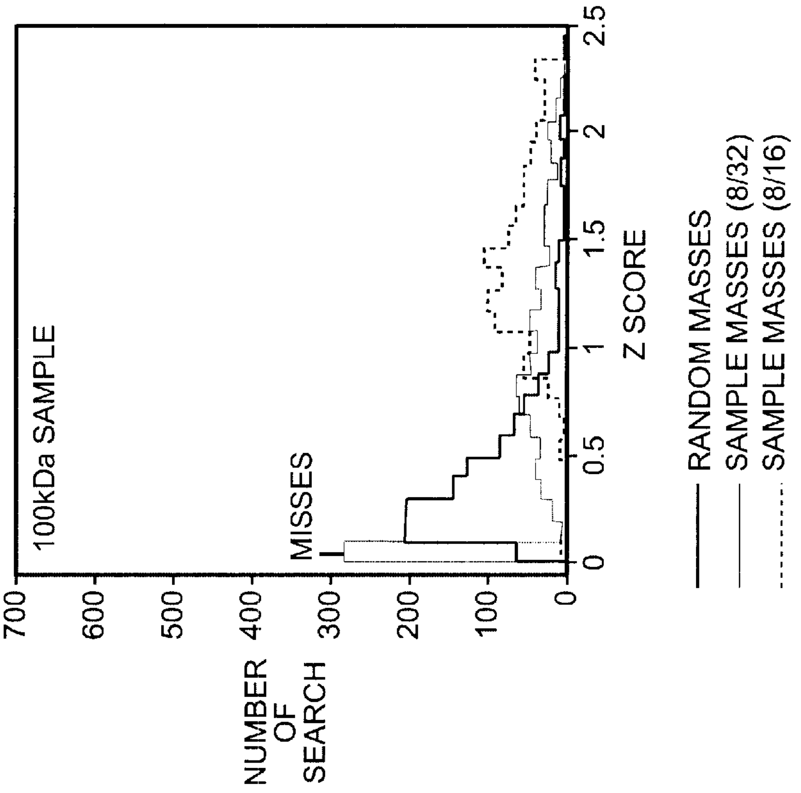
FIGS. 9–21: Graphs of the results of the simulations discussed in the Examples.

In one embodiment the invention provides a method for determining the probability that a biological molecule identification is incorrect for a chosen significance level. For the purposes of this invention, the identification is the result obtained for an unknown biological molecule after a search of known biological molecules. So, for example, a protein identification is the result obtained for an unknown protein after a search of known proteins; that is, the protein identification is a known protein which is identified as being the unknown protein.

Biological molecules include any biological polymer that can be degraded into constituent parts. The degradation is preferably into constituent parts at predictable positions to form predictable masses. Examples of biological molecules include proteins, nucleic acid molecules, polysaccharides and carbohydrates.

Proteins are polymers of amino acids. Constituent parts of proteins comprise amino acids. A protein typically contains approximately at least ten amino acids, preferably at least fifty amino acids and more preferably at least 100 amino acids.

Nucleic acids are polymers of nucleotides. Constituent parts of nucleic acids comprise nucleotides. Typically, a nucleic acid contains at least 100 nucleotides, preferably at least 500 nucleotides.

Polysaccharides are polymers of monosaccharides. Constituent parts of polysaccharides comprise one or more monosaccharides. Typically, a polysaccharide contains at least five monosaccharides, preferably at least ten monosaccharides.

Mass data of biological molecules are quantifiable information about the masses of the constituent parts of the biological molecule. Mass data include individual mass spectra and groups of mass spectra. The mass spectra can be in the form of peptide maps, oglionucleotide maps or oligosaccharide maps.

Mass data for proteins can be generated in any manner which provides mass data within a certain accuracy. Examples include matrix-assisted laser desorption/ionization mass spectrometry, electrospray ionization mass spectrometry, chromatography and electrophoresis. Mass data can also be generated by a general purpose computer configured by software or otherwise.

For the purposes of the present invention the mass data, for example a peptide mass, $m_i$, is determined to an accuracy $\pm\Delta m_i$, with $\Delta m_i/m_i$ preferably <10,000 ppm, more preferably <100 ppm and most preferably <30 ppm.

A step in generating mass data of a biological molecule may include first cleaving the biological molecule into constituent parts. Biological molecules may be cleaved by methods known in the art. Preferably, the biological molecules are cleaved into constituent parts at predictable positions to form predictable masses. Methods of cleaving include chemical degradation of the biological molecules. Biological molecules may be degraded by contacting the biological molecule with any chemical substance.

For example, proteins may be predictably degraded into peptides by means of cyanogen bromide and enzymes, such as trypsin, endoproteinase Asp-N, V8 protease, endoproteinase Arg-C, etc. Nucleic acids may be predictably degraded into constituent parts by means of restriction endonucleases, such as Eco RI, Sma I, BamH I, Hinc II, etc. Polysaccharides may be degraded into constituent parts by means of enzymes, such as maltase, amylase, alpha-mannosidase, etc.

The invention relates to improving current methods for identifying biological molecules by adding to current methods a non-computationally intensive method of evaluating the quality of the identification. Current methods for identifying biological molecules as well as the methods of the present invention will be described for protein identification. These methods are equally applicable to any biological molecule.

Current methods used to identify unknown proteins are typically similar to that illustrated in FIG. 1, but with the addition of database searching. The unknown protein is first cleaved into its constituent parts, as described above. The masses of the resulting constituent parts are analyzed and experimental mass data are generated. The determined masses are then compared with theoretical mass data generated for polypeptide sequences of a DNA (genome, cDNA, or otherwise) and/or protein database. Typically, the masses in a database are from a single organism. Additionally, an unknown protein to be identified can be in a mixture of proteins.

A biological molecule database is any compilation of information about characteristics of biological molecules. Databases are the preferred method for storing both polypeptide amino acid sequences and the nucleic acid sequences that code for these polypeptides. The databases come in a variety of different types that have advantages and disadvantages when viewed as the hypothesis for a polypeptide identification experiment.

While the "database entry" for an amino acid sequence may appear to be a simple text file to a user browsing for a particular polypeptide, many databases are organized into very flexible, complicated structures. The detailed implementation of the database on a particular system may be based on a collection of simple text files (a "flat-file" database), a collection of tables (a "relational" database), or it may be organized around concepts that stem from the idea of a protein, gene, or organism (an "object-oriented" database).

Protein mass data may be predicted from nucleic acid sequence databases. Alternatively, protein mass data may be obtained directly from protein sequence databases which contain a collection of amino acid sequences represented by a string of single-letter or three-letter codes for the residues in a polypeptide, starting at the N-terminus of the sequence. These codes may contain nonstandard characters to indicate ambiguity at a particular site (such as "B" indicating that the residue may be "D" (aspartic acid) or "N" (asparagine). The sequences typically have a unique number-letter combination associated with them that is used internally by the database to identify the sequence, usually referred to as the accession number for the sequence.

Databases may contain a combination of amino acid sequences, comments, literature references, and notes on known posttranslational modifications to the sequence. A database that contains these elements is referred to as "annotated." Annotated databases are used if some functional or structural information is known about the mature protein, as opposed to a sequence that is known only from the translation of a stretch of nucleic acid sequence. Non-annotated databases only contain the sequence, an accession number, and a descriptive title.

In general, each comparison of the unknown protein with the database proteins is assigned a score on the basis of a reasonable algorithm. Algorithms, discussed below, exist that measure the probability that a particular sequence could give rise to the experimental results.

Comparisons can be made and scores can be generated by a general purpose computer configured by software or otherwise. The unknown protein is then "identified" with a sequence that produces a score having a high degree of similarity.

More specifically, a score is a measure of the degree of similarity between the theoretical mass data of a database protein and the experimental mass data of an unknown protein for the same experimental conditions. The experimental mass data is the mass data that was generated and measured for the unknown protein under particular experimental conditions. The experimental conditions under which an unknown protein and the proteins from the database are handled should be the same.

Experimental conditions include the manner in which cleavage of the proteins is accomplished, that is, the specific substance used for the chemical degradation of the proteins. Additionally, the experimental condition defines the efficiency of the chemical degradation. The efficiency of a chemical degradation specifies the number of potential cleavage sites that may be expected to remain uncleaved. The mass data generated from the protein database may include mass data representing proteins with incomplete cleavages. Experimental conditions also include the method by which the mass data is generated.

Scores which denote a high degree of similarity are usually the top twenty scores generated in a comparison, more preferably the top ten scores, even more preferably the top five scores and most preferably the top one score.

A similarity between a group of experimental masses of the unknown protein and a group of theoretical masses of a database protein is assessed by comparing every experimental mass with every theoretical mass. A simple algorithm for the measure of similarity is the number of experimental masses that are similar to at least one theoretical mass. For example, the masses of an experimental peptide map of an enzymatically digested unknown protein can be compared with the theoretical masses calculated by applying the rules for the specificity of the enzyme to the amino acid sequence of a database protein.

More sophisticated algorithms can be used to generate a score. For example, ProFound (ProteoMetrics) is a software tool for searching protein sequence databases. ProFound measures similarity using a Bayesian statistical framework.

In the present invention an experimental mass data of an unknown protein and one of the mass data of the proteins of the database are said to be similar if the absolute value of the difference between them is less than the uncertainty in the measurement.

The similarity between the mass data of the unknown protein and each of the theoretical mass data of the database proteins is assessed taking into account the accuracy of the determination of the mass data by a particular method. For example, mass spectrometry determines a peptide mass $m_i$ to an accuracy of $\pm\Delta m_i$, with $\Delta m_i/m_i$ typically >30 ppm. Therefore, within the mass range $m_i \pm \Delta m_i$ peptide masses of several proteins in the database are considered to match the unknown protein.

The observed molecular mass or the observed isoelectric point of a protein can be used in combination with the measured masses of peptides generated by proteolysis to constrain the search for a polypeptide. In particular, the comparison between the theoretical mass data of the database proteins and the mass data of the unknown protein may be constrained to only those proteins of the database which are within a chosen mass range. The chosen mass range is preferably within 50% of the mass of the unknown protein, more preferably within 35%, most preferably within 25%.

Similarly, the comparison between the theoretical mass data of the database proteins and the mass data of the unknown protein may be constrained to only those proteins of the database which are within a chosen isoelectric point range. The isoelectric point (pI) of a protein is the pH at which its net charge is zero. The chosen isoelectric point range is preferably within 50% of the isoelectric point of the unknown protein, more preferably within 35%, most preferably within 25%.

Using the observed molecular mass or isoelectric point of a polypeptide to constrain a search must be done carefully. When nonannotated nucleotide sequence databases are used (such as TREMBL or GENPEPT), subsequent processing can greatly alter the pI or molecular mass of a protein, so much so that no identification can be made. For example, the small, highly conserved protein ubiquitin (SWISSPROT accession number P02248) has a molecular mass of 8.6 kD, which is the mass that would be measured by a mass spectrometer or a gel. A simple keyword search of the translated-nucleotide database GENPEPT results in several sequences for the same protein [accession numbers M26880 (77 kD), U49869 (25.8 kD) and X63237 (17.9 kD)]. None of these nucleotide-translated sequences give the correct molecular mass or pI, so using those parameters to limit a search would result in missing the database sequence altogether. Only annotated databases that fully outline known modifications can be used when the properties of the mature protein are being used to constrain a search.

Biological molecules may undergo common modifications in their structure. The mass data that are generated from a biological molecule database may include mass data representing biological molecules with common modifications.

Examples of such modifications are posttranslational modifications of proteins. The modification state of a protein is usually not known in detail. In database searches, it can be useful to assume that some common modifications might be present. This is achieved by comparing the measured peptides masses of the unknown protein with both the masses of the unmodified and modified peptides in the database.

Examples of posttranslational modifications include glycosylation and the oxidation of the amino acid methionine. Another example is the phosphorylation of the amino acids serine, threonine, and tyrosine. Phosphorylation is often used to activate or deactivate proteins and the phosphorylation state of an experimentally observed protein depends on may factors including the phase of the cell cycle and environmental factors.

Optionally, further information of the unknown protein's sequence is obtained by generating fragment mass data. Fragment mass data for a peptide can be generated in any manner which provides fragment mass data within a certain accuracy. Experimental conditions include the type of energy used to generate the fragment mass data. Vibrational excitation energy can be used. The vibrational excitation may be generated by collisions of the peptide with electrons, photons, gas molecules or a surface. Electronic excitation can be used. The electronic excitation may be generated by collisions of the peptide with electrons, photons, gas molecules (e.g. argon) or a surface.

In another example, the experimental fragment mass spectrum of a peptide from an enzymatically digested unknown protein is compared with the theoretical masses calculated by applying the rules for the specificity of the enzyme, and the rules for the fragmentation as known to those of ordinary skill in the art, to the amino acid sequence of a database protein. For example, the software tool PepFrag (ProteoMetrics) allows for searching protein or nucleotide sequence databases using a combination of mass spectra data and fragmentation mass spectra data.

Fragment mass data for the purposes of this invention can be generated by using multidimensional mass spectrometry (MS/MS), also known as tandem mass spectrometry. A number of types of mass spectrometers can be used including a triple-quadruple mass spectrometer, a Fourier-transform cyclotron resonance mass spectrometer, a tandem time-of-flight mass spectrometer, and a quadruple ion trap mass spectrometer. A single peptide from a protein digest is subjected to MS/MS measurement and the observed pattern of fragment ions is compared to the patterns of fragment ions predicted from database sequences.

All of the protein identification strategies outlined above to generate a score are currently available as CGI programs that can be accessed using a browser.

There is a risk of false identification of the unknown protein for several reasons. For example, each proteolytic peptide mass measured can be found in several proteins in a genome database. Also for example, a peptide map is often incomplete with respect to the protein identified and can contain a background of proteolytic peptide masses from other proteins. An identification of a protein is definitely uncertain if the result is characterized by a score that could as well be due to random matching between the peptide map and a protein in the database.

This invention provides a method of determining the probability that a biological molecule identification is not true for a chosen significance level based on a comparison between theoretical mass data and experimental mass data.

The method comprises generating theoretical mass data for a particular experimental condition for known proteins from a protein sequence database as described above. Experimental mass data for an unknown protein for the same experimental condition is also generated.

The experimental mass data, and optionally fragment mass data, generated for the unknown protein is compared with the theoretical data generated for each known protein in the database. The comparisons are carried out as described above. The protein identifications are hypothesized to be false and random. A score is calculated for each comparison. The score is a function of the similarity between each of the theoretical mass data as compared with the experimental mass data of the unknown protein. Each protein in the database can be referred to as a candidate to which a score is assigned.

FIG. 4 is a frequency distribution that resulted from a sample database search. The horizontal axis represents the magnitude of the resulting score; and, the vertical axis represents the frequency of the occurrence of a particular score. Therefore, it follows that the candidates in the right end or right "tail," of the distribution, in general, are more similar to the unknown protein than the rest of the candidates. In other words, this "tail" contains candidates that have the greatest possibility to contain the correct protein match.

FIG. 5 is a plausible description of the distributions underlying the graph in FIG. 4. The description of FIG. 5 is based on the assumption that the distribution of FIG. 4 is made up of a number of small normal distributions. Within each of these small normal distributions are candidates that have similar properties to one another, such as the number of matched masses.

It follows that the right "tail" of FIG. 4 can similarly be described by a small normal distribution, as depicted in the right most normal distribution in FIG. 5. The normal distribution that describes the "tail" represents the entire collection of scores that would result from the comparison of a particular unknown protein with any and all other proteins. This collection of scores can be referred as a population. Population parameters (i.e., mean and standard deviation) of this "tail" are estimated by the method that follows.

First, at least two scores are selected, from the scores generated by the mass data comparisons, to form a primary data set. Preferably, the scores that are selected are the scores that denote a high degree of similarity between the theoretical mass data generated for the known proteins and the experimental mass data generated for the unknown protein. Preferably the number of scores selected to form the primary data set are in the range from about 2 to about 200 scores, more preferably from about 5 to about 50 scores, and most preferably from about 3 to about 25 scores.

Secondly, a sufficient quantity of artificial data sets are generated from the primary data set. The artificial data sets are generated using methods known in the art. Such methods include bootstrapping or jackknifing, as described below. A sufficient quantity of artificial data sets may, for example, be in the range of about 1 to $10^{10}$, preferably 10 to $10^9$, more preferably 50 to $10^8$ and most preferably from about 100 to about $10^7$.

In a preferred embodiment of the bootstrap method, the artificial data sets have the same number of members as the primary data set. These members are selected at random, with replacement, from the primary data set. Thus, each artificial data set has a variation of members of the primary data set, where in which some members of the primary data set may not appear at all and other members may appear more than once. FIG. 6 is a graph of a sample bootstrapping expected distribution. There, 1000 artificial data sets were generated from a primary data set. The primary data set and the 1000 artificial data sets each consist of four members.

In another embodiment of the bootstrap method, the artificial data sets can each have a fewer number of members than the primary data set. Also, the number of members in each artificial data set can vary from each other.

In the jackknife method, the artificial data sets are subsets of the primary data set. Preferably the number of members in the subsets is one less than the number of members in the primary data set. Preferably every possible subset is used. In another embodiment of the jackknife method, the subsets can each have more than one less member as compared with the number of members in the primary data set. Also, the number of members in each of the subsets can vary from one another.

A sample mean is calculated for each artificial data set by the formula described below:

$$\bar{x} = \sum_{i=1}^{n} \left(\frac{x_i}{n}\right)$$

wherein $x_i$ is an member of a particular artificial data set and n is the number of members in that particular artificial data set.

The sample means generated by the artificial data sets forms a normal distribution if the number of sample means is large. These sample means are used to estimate the population mean and population standard deviation. The population, for which these statistics are estimated, is based on the distribution underlying the primary data set. The following formulas are used for the estimation:

$$\sum_{i=1}^{n} \left(\frac{\bar{x}_i}{n}\right) = \mu \qquad \sqrt{\sum_{i=1}^{n} \frac{(\bar{x}_i - \mu)^2}{n}} = \sigma$$

where $\bar{x}_i$ is the sample mean from each of the n artificial data sets; and n is the number of artificial data sets.

The population mean ($\mu$) and population standard deviation ($\sigma$) are used to calculate a Z score for each of the scores that were generated by the database comparison. Therefore, a Z score is associated with each of the candidates. The Z score is a measure of the distance in standard deviation units of a sample from the population mean. It is defined as follows:

$$Z_i = (x_i - \mu)/\sigma,$$

where i=1, 2, . . . n

Here $x_i$ is each of the scores generated by the database comparisons; and n is the number of scores.

The hypothesis used in the present invention is that all the protein identifications are random matches (i.e., incorrect identifications). However, for each protein identification there is a different probability that this hypothesis is true. So at a certain probability it can be considered reasonable to reject the hypothesis. This probability is termed a significance level. In other words, a significance level is the probability used as the criterion for rejecting the hypothesis. The significance level may be any value in the range from about from 0.0001 to about 0.1, more preferably in the range from about 0.001 to about 0.05. So, for example, if 0.05 is chosen as the significance level then there is only a 5% probability of being incorrect when considering a protein identification to be a random match.

When considering what significance level should be chosen a number of parameters can be assessed, such as the number of masses in the peptide map, the mass accuracy, the degree of incomplete enzymatic cleavage, the protein mass range, and the size of the genome.

A general feature of significance testing is that as the significance level is decreased, the relative frequency of random, incorrect matches considered to be nonrandom matches (i.e., a correct identification) is expected to decrease, and the relative frequency of nonrandom matches considered to be random matches is expected to increase.

Significance level can be expressed in terms of Z score. Therefore, the Z score, like the significance level, indicates the probability that an identification is a random match. For example, a Z score of 1.65 (or lower) indicates that the identification is likely (with 95% confidence) to be a random match. Also, since the Z score is in normalized units, the associated significance level will be the same regardless of the size of the database examined.

Therefore, the present invention can determine the probability that a particular protein identification is a random match for a chosen significance level. First the Z score corresponding to the identification of interest is calculated. Such a score is termed the test Z score. The test Z score is compared to the Z score corresponding to the chosen significance level. The Z score corresponding to the chosen significance level is termed the critical Z score or $Z_C$. If the test score falls to the left of the critical Z score on the horizontal axis (see FIG. 7), then the identification is considered likely to be a random match. In other words, the probability that the protein identification is incorrect is high.

Significance testing has the potential to be used as a quick check for determining whether an identification is likely to be a random match. However, significance testing can never tell if a result is correct or incorrect. Only biological methods have the potential of showing if a protein identification result is true.

In one embodiment of the present invention a protein identification can be conducted where in which the mass data of the unknown protein is compared with groups of selected amino acids (instead of compared with known proteins in a database). A group of amino acids is a set of amino acids. The molecular weight of the unknown protein is calculated. Groups of amino acids are selected to form proteins which have a similar molecular weight to the unknown protein. A molecular weight is considered to be similar if it is substantially identical to the molecular weight of the unknown protein within a preselected range. Mass data are generated for these proteins and the unknown protein. Comparisons of the mass data and Z score evaluations are conducted as described above.

As discussed above, the Z score can be used as an indicator of the quality of a search result. The criterion for significance in terms of Z score is a uniform standard. For example, the user can set the same criterion for different database searches (i.e., databases of different sizes or species). This invention provides significance testing which is quick, fully automated and readily integrated with database searching software used for protein identification.

It is to be appreciated that the methods or algorithms of the present invention described herein above may be performed using a general purpose computer or processing system which is capable of running application software programs, such as an IBM personal computer (PC) or suitable equivalent thereof. Preferably, the application program code is embedded in a computer readable medium, such as a floppy disk or computer compact disk (CD). Furthermore, the computer readable medium may be in the form of a hard disk or memory (e.g., random access memory or read only memory) included in the general purpose computer.

As appreciated by one skilled in the art, the computer software code may be written, using any suitable programming language, for example, C or Pascal, to configure the computer to perform the methods of the present invention. While it is preferred that a computer program be used to accomplish any of the methods of the present invention, it is similarly contemplated that the computer may be utilized to perform only a certain specific step or task in an overall method, as determined by the user.

Preferably, the methods of the present invention are used with one or more displays (e.g., conventional CRT or liquid crystal display) provided with the processing system for presenting an indication of, for example, the final result of the process or algorithm. The display may preferably be utilized to present such information graphically (e.g., charts or three dimensional models of biological molecules) for further clarity.

In addition to performing the necessary calculations and processing functions in accordance with the present invention, the general purpose computer may also be used, for example, to store data pertaining to known biological molecules corresponding to a predetermined experimental condition. Such information may be stored on a hard disk or other memory, either volatile or non-volatile, included in the computer. Similarly, the information may be stored on a computer readable medium, such as floppy disk or CD, which can be transported for use on another computer system, as appreciated by those skilled in the art. In this manner, the methods of the present invention may be performed on any suitable general purpose computer and are not limited to a dedicated system.

Those of ordinary skill in the art will recognize that the present invention has wide applicability for identification of unknown biological molecules. Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the present invention.

EXAMPLES

The Z score is a measure of the distance in standard deviations of a sample from the mean. It is defined as:

$$Z=(x-\bar{x})/\sigma$$

where x is a Gaussian random variable, $\bar{x}$ is the mean of x, and $\sigma$ is the standard deviation of the distribution of x.

In this study, Z is used to indicate the likelihood that a candidate belongs to a random match population in the sense of traditional statistics. For example, a Z score of 1.65 (or lower) indicates that the candidate is likely (with 95% confidence) to be a random match. In our database search, the ProFound search engine is used to calculate the Bayesian probability for each candidate sequence to be the protein being analyzed. Then, the Z score is calculated based on the probability value for each candidate.

Simulation

A Monte Carlo simulation was used to determine the distribution of the estimated Z scores for top candidates in two situations. In the first situation (the random mass group), the data set consists of randomly chosen monoisotopic peptide masses from theoretical tryptic digests of entries in the NCBI nr sequence database. In the second situation (the sample mass group), the data set consists of peptide masses chosen from a given protein's theoretical tryptic digests and random masses from theoretical tryptic digests of the nr database.

Both the sample and random mass groups contain 1,000 mass data sets.

Simulation Variables

For a given protein sequence, 8, 12 and 16 authentic monoisotopic peptide masses were chosen, and in each case a 2 or 4 fold higher number of random masses was added. Four specific sequences for proteins with molecular masses of respectively 50, 100, 200 and 400 kDa were chosen.

TABLE 1

Summary of simulation variables

Figure 9:
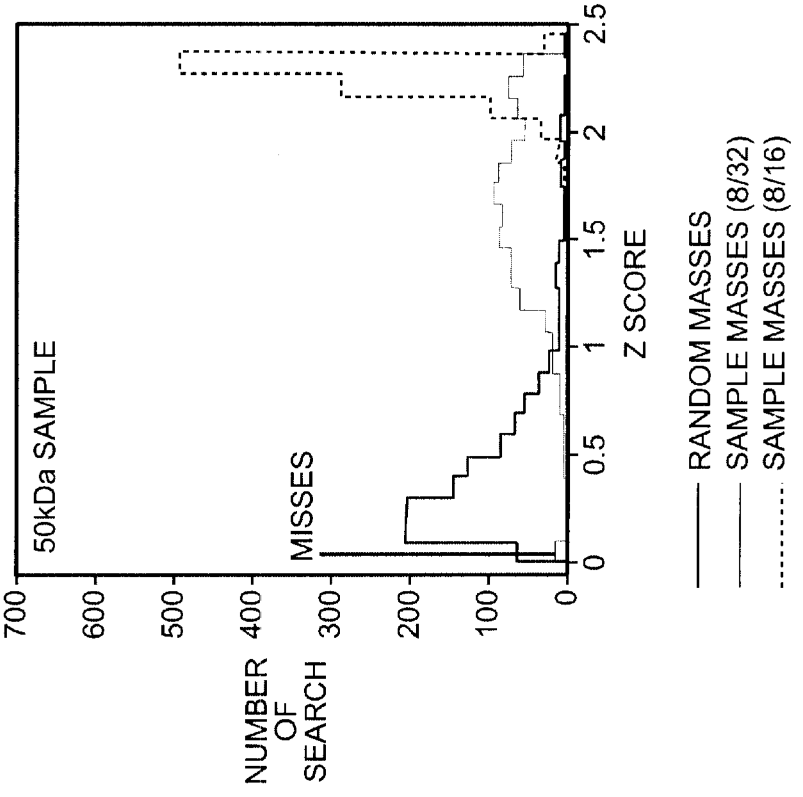
Figure 11:
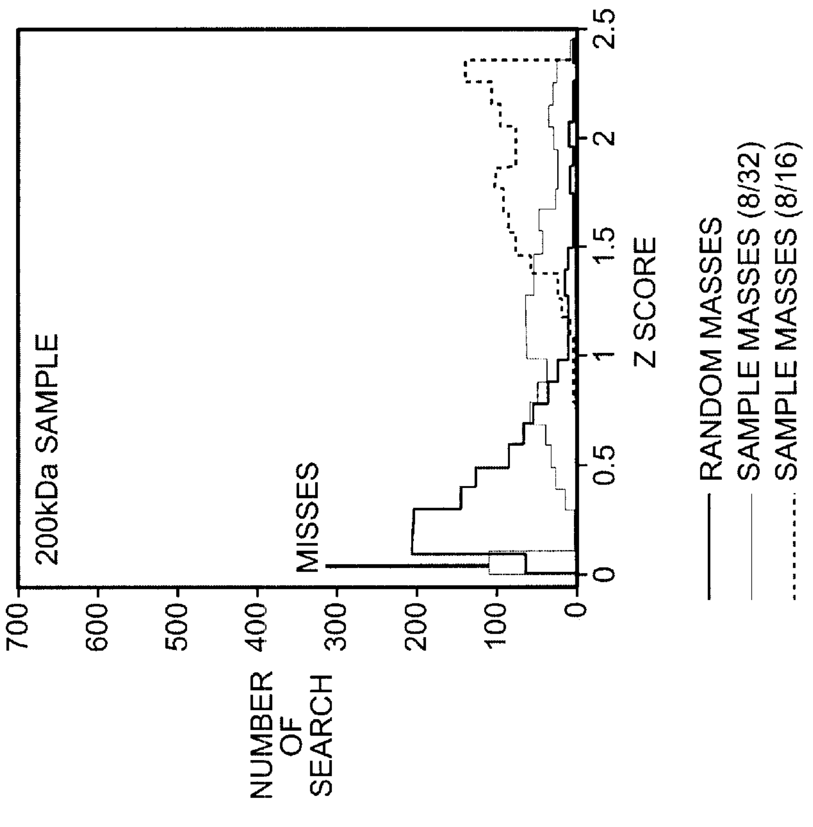
Figure 12:
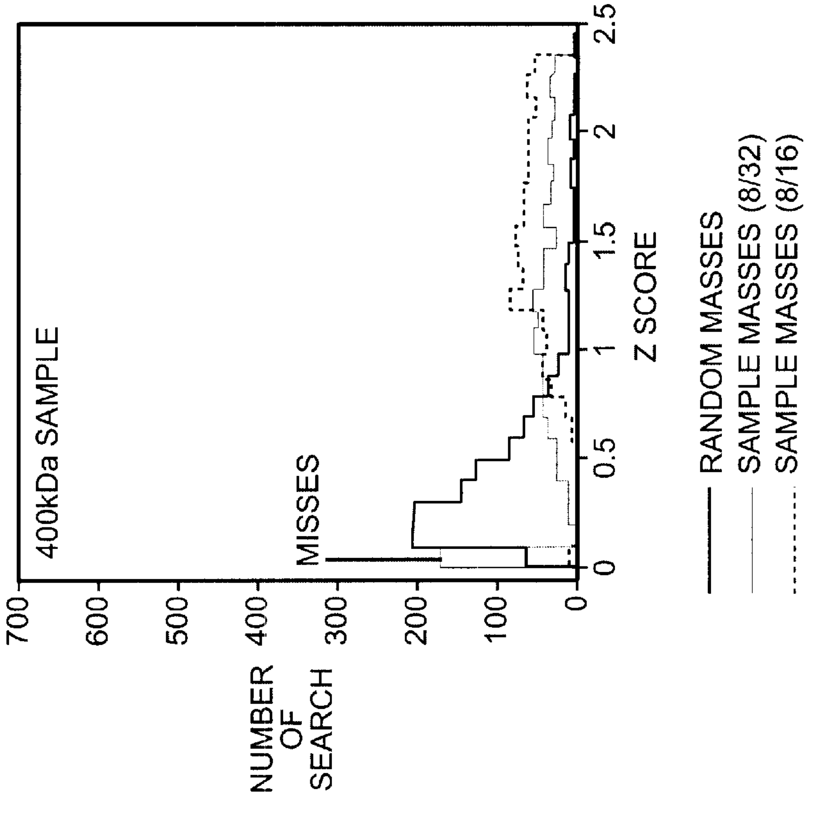
Figure 13:
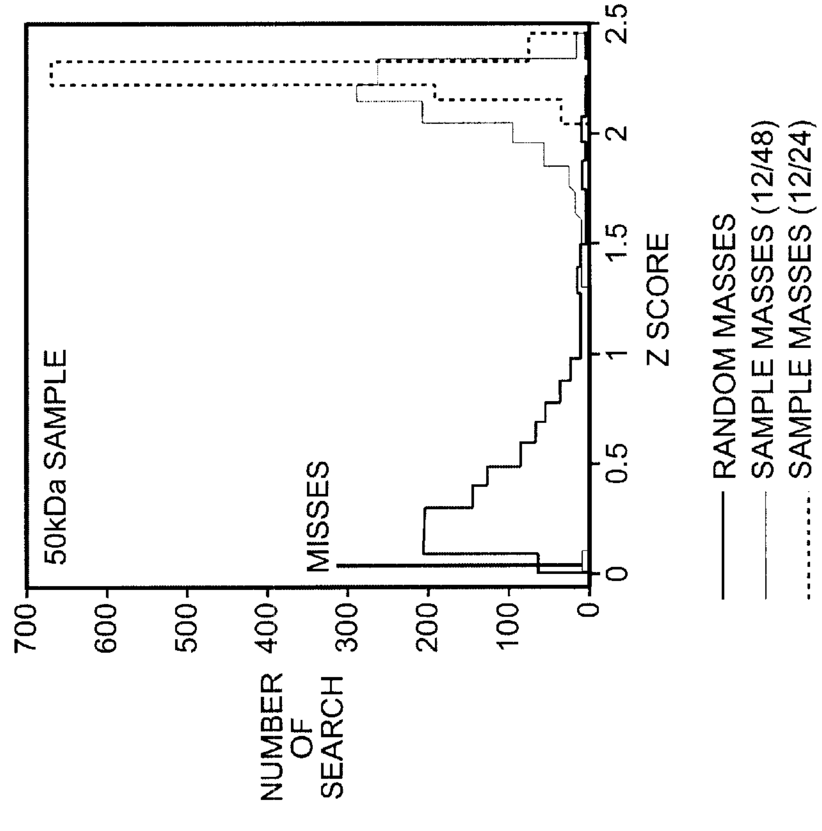
Figure 14:
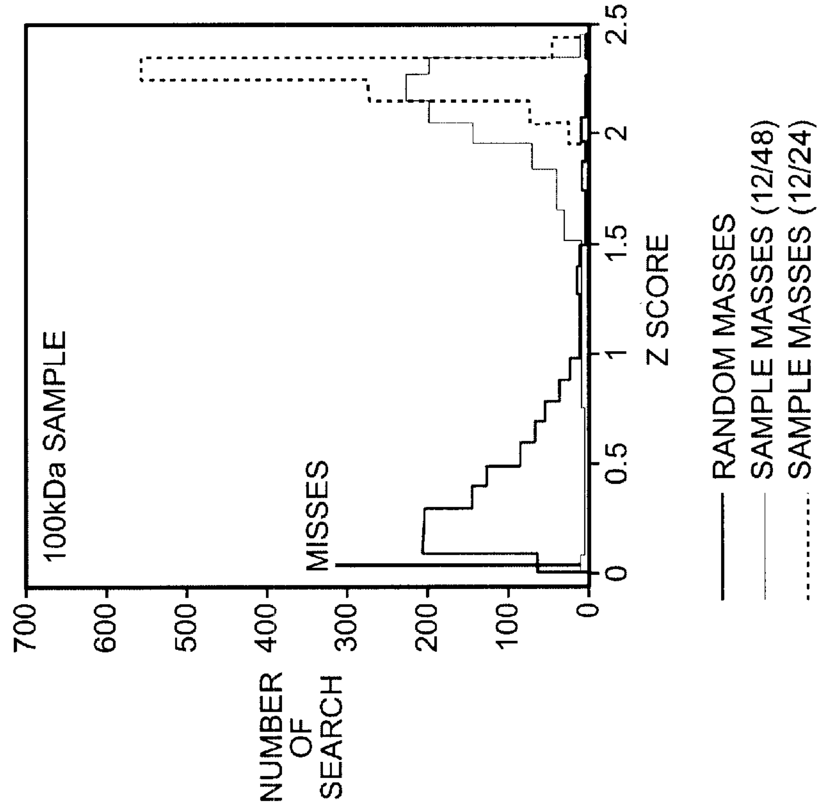
Figure 15:
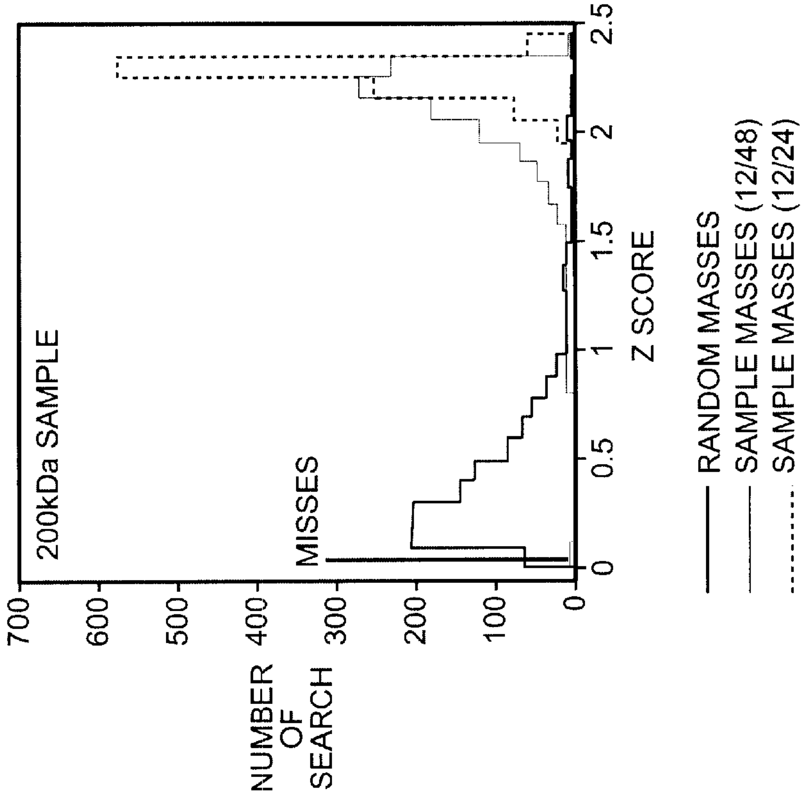
Figure 16:
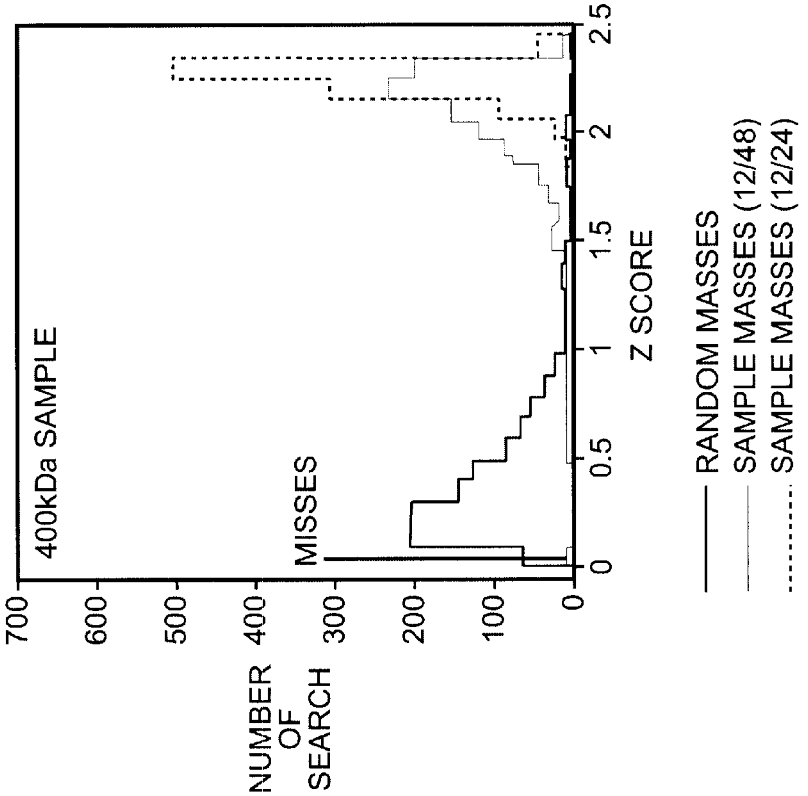
Figure 18:
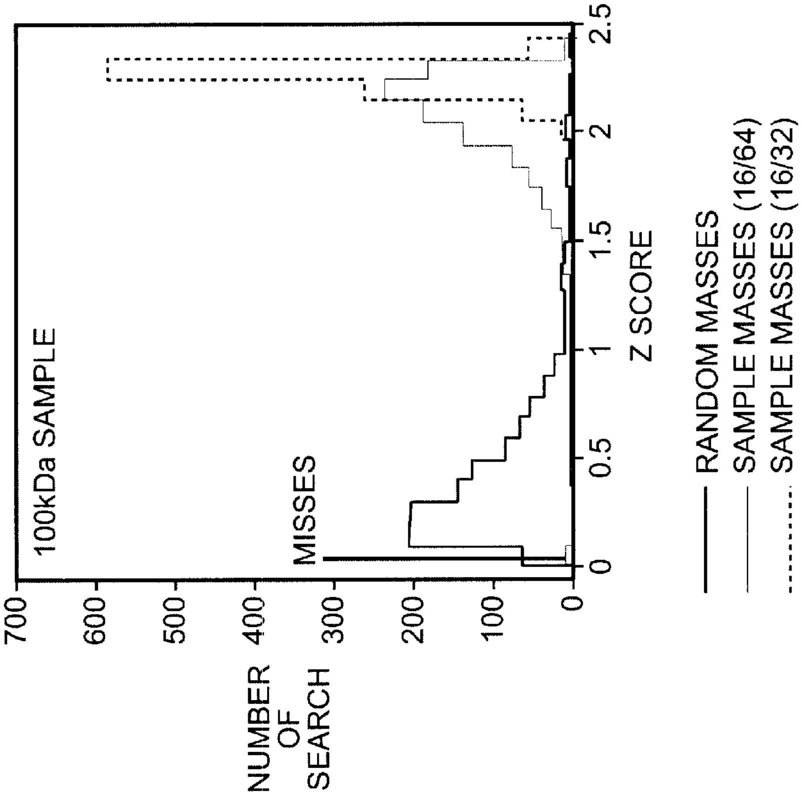
Figure 17:
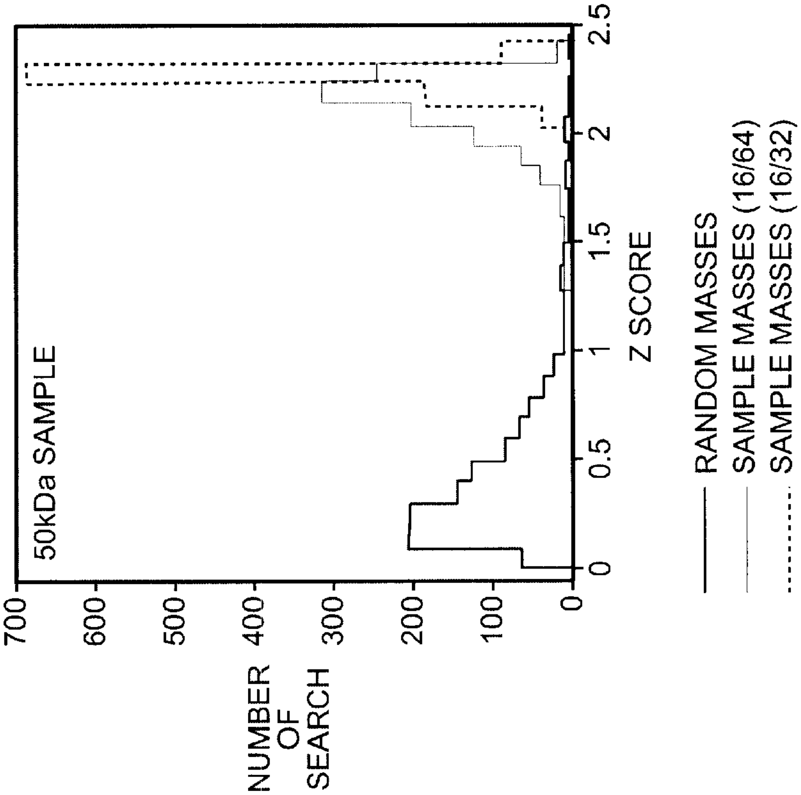
Figure 19:
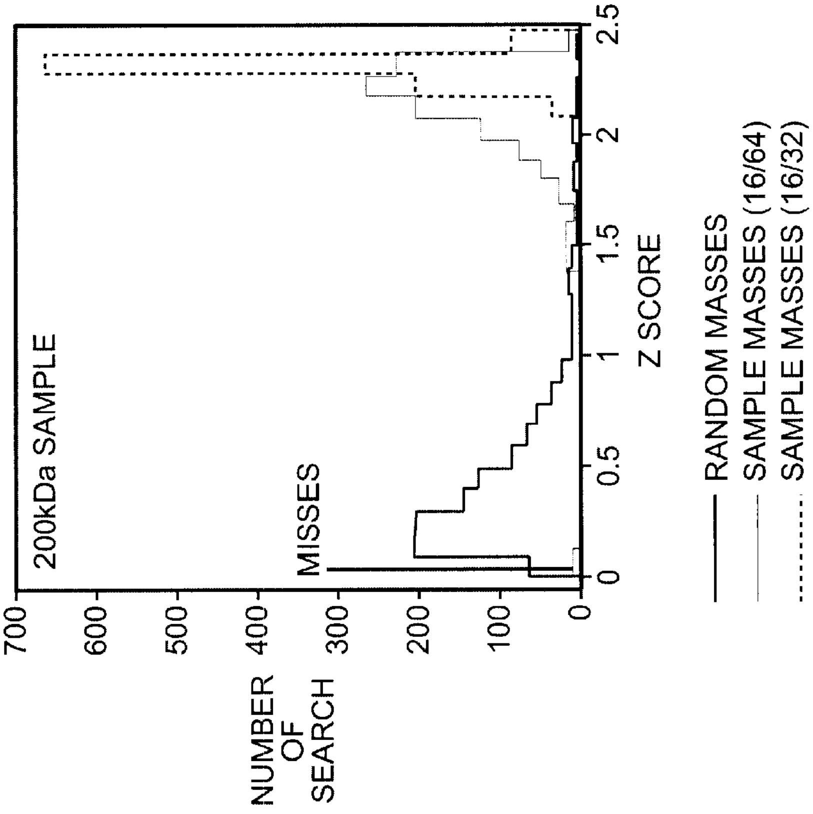
Figure 20:
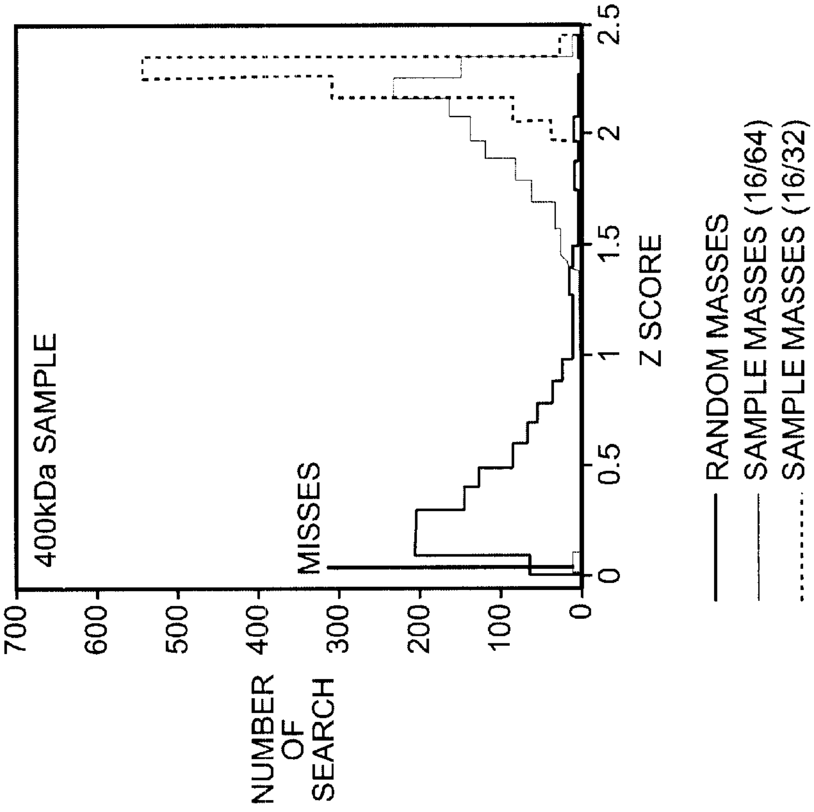

| | Protein Mass (kDa) | | | |
|---|---|---|---|---|
| Sample/Random | 50 | 100 | 200 | 400 |
| 8/32<br>8/16 | FIG. 2 | FIG. 3 | FIG. 4 | FIG. 5 |
| 12/48<br>12/24 | FIG. 6 | FIG. 7 | FIG. 8 | FIG. 9 |
| 16/64<br>16/32 | FIG. 10 | FIG. 11 | FIG. 12 | FIG. 13 |

Search Parameters

All taxa (or explicitly noted), 50 ppm mass error tolerance, 1 missed cleavage site, no modification.

Search with Experimental Data

A number of experimentally obtained data sets were also used in this study.

Simulation: Sample and Random Mass Groups

FIGS. 9–20 are the results of simulation shown as histograms of estimated Zs for the top candidates. There are three curves in each plot. One curve represents the random mass group. Since the masses in these data sets are random, the top candidates are random hits. The curve is biased toward lower Z values. The other two curves are for data sets containing peptide masses from a known protein sequence, with the number of random masses being 4 or 2 fold higher than the number of sample masses. The top candidates are the known protein sequence. The curves are toward higher Z side. The number of searches where the known protein is not top candidate is plotted at Z=0 and indicated by "Misses."

The distributions of estimated Z scores for the authentic sample mass group and the random mass group are separated by the resolving power of the ProFound search engine. The separation is clearer when the number of sample peptides from the known protein increases and the number of random masses decreases. Note that the distributions show general trends across the mass range (50–400 kDa) of known proteins, when the number of peptide masses from the known protein and number of random masses are fixed. This result indicates that the estimated Z value is not very sensitive to the molecular mass of the proteins to be identified.

Simulation: on Different Databases

To explore the effect of different database (sizes, species) on the estimated Z of the random mass group, we also compared the Z score distributions for simulations on all taxa, primate and fungi sequence databases with the same random mass group of data sets. FIG. 8 shows a strong similarity in Z distributions. This similarity allows the user to set the same criterion for significance test across different databases and over time (i.e. as the database size increases over time).

Experimental Data

Figure 21:
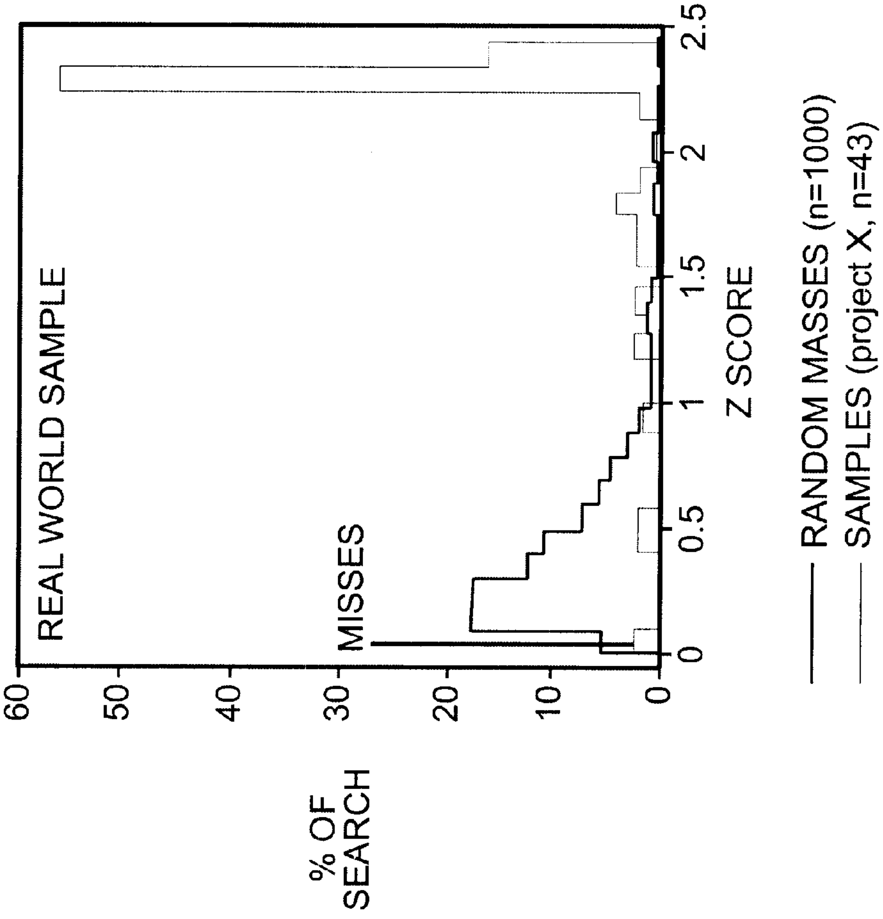

FIG. 21 shows the estimated Z score distribution for experimental data sets, together with the Z score distribution for random mass group as comparison. The correctness of the identifications was checked using independent procedures, including MS/MS. The distribution for experimental data sets is toward higher Z side.

We claim:

1. A method for determining the probability that a biological molecule identification is incorrect for a chosen significance level and for a particular experimental condition, the method comprising:

a) generating theoretical mass data for biological molecules;

b) generating an experimental mass data for an unknown biological molecule;

c) comparing the experimental mass data generated in step (b) with each theoretical mass data generated in step (a);

d) calculating a score for each comparison in step (c), wherein the score is a function of the similarity between each of the data generated in step (a) and the data generated in step (b);

e) selecting at least two scores from the scores in step (d) to form a primary data set, wherein the scores correspond to a comparison that denotes a degree of similarity between each of the data generated in step (a) and the data generated in step (b);

f) generating a sufficient quantity of artificial data sets from the primary data set in step (e);

g) calculating a sample mean for each artificial data set in step (f);

h) estimating population mean and population standard deviation from the sample means generated in step (g); wherein the population is based on the distribution underlying the primary dataset;

i) computing a Z score from the population mean and population standard deviation for each score calculated in step (d) to standardize the scores;

j) choosing a significance level; and k) comparing a test Z score to a Z score of the chosen significance level to determine the probability that the biological molecule identification is incorrect.

2. The method according to claim 1 wherein the number of scores selected in step (e) to form the primary data set is in the range from about 2 to about 500.

3. The method according to claim 1 wherein the number of scores selected in step (e) to form the primary data set is in the range from about 3 to about 25.

4. The method according to claim 1 wherein the unknown biological molecule is in a mixture of biological molecules.

5. The method according to claim 1 wherein the mass data generated in step (a) is mass data from a biological molecule database.

6. The method according to claim 1 wherein the mass data generated in step (a) is mass data generated from selected amino acid groups which can correspond to the mass data of an unknown biological molecule.

7. The method according to claim 1 wherein the artificial data sets in step (f) are generated by a method comprising selecting with replacement the scores from the primary data set generated in step (e).

8. The method according to claim 7 wherein the number of scores in each artificial data set is equal to the number of scores in the primary data set.

9. The method according to claim 1 wherein the artificial data sets in step (f) are generated by a method comprising selecting subsets of the scores from the primary data set generated in step (e).

10. The method according to claim 9 wherein the number of scores in each subset is equal to one less than the number of scores in the primary data set.

11. The method according to claim 1 wherein a sufficient quantity of artificial data sets is in the range from about 1 to about $10^{10}$.

12. The method according to claim 1 wherein the mass data in step (a) are generated by a computer.

13. The method according to claim 1 wherein the mass data in step (b) is generated by a computer.

14. The method according to claim 1 wherein the mass data in step (b) is generated by a mass spectrometer.

15. The method of claim 1 wherein the biological molecules are proteins.

16. The method of claim 1 wherein the biological molecules are nucleic acid molecules.

17. The method of claim 1 wherein the biological molecules are polysaccharides.

18. The method according to claim 1 wherein a sufficient quantity is in the range of from about 50 to about $10^8$ artificial data sets.

19. The method according to claim 1 wherein a sufficient quantity is in the range of from about 100 to about $10^7$ artificial data sets.

20. The method according to claim 1 wherein the experimental condition defines the mass data as resulting from chemical degradation of the biological molecules.

21. The method according to claim 20 wherein the chemical degradation is enzymatic digestion.

22. The method according to claim 20 wherein the experimental condition defines an efficiency of the chemical degradation.

23. The method of claim 21 wherein the enzymatic digestion is by trypsin.

24. The method according to claim 1 wherein the comparison in step (c) is constrained to known biological molecules within a chosen mass range.

25. The method according to claim 1 wherein the comparison in step (c) is constrained to known biological molecules within a chosen isoelectric point range.

26. The method according to claim 1 wherein the experimental condition defines a particular accuracy for mass data determination.

27. The method according to claim 1 wherein the comparison in step (c) comprises known biological molecules which exhibit modifications.

28. The method according to claim 27 wherein the modifications of the biological molecules are posttranslational modifications of proteins.

29. The method according to claim 1 wherein fragment mass data is generated for at least one constituent part of the biological molecules.

30. The method according to claim 29 wherein the comparison between the mass data comprises the comparison of the fragment mass data.

31. The method according to claim 29 wherein the experimental condition defines the energy used to generate the fragment mass data.

32. The method according to claim 24 wherein the chosen mass range is within 25% of the mass of the unknown biological molecule.

33. The method according to claim 24 wherein the chosen mass range is within from about 0.1 to about 3000 kDa.

34. The method according to claim 25 wherein the isoelectric point range is within 25% of the bioelectric point of the unknown biological molecule.

35. The method according to claim 31 wherein the energy used to generate the fragment mass data is vibrational excitation.

36. The method according to claim 31 wherein the energy used to generate the fragment mass data is electronic excitation.

37. The method according to claim 35 wherein the vibrational excitation is generated by collisions with electrons, photons, gas molecules or a surface.

38. The method according to claim 36 wherein the electronic excitation is generated by collisions with electrons, photons, gas molecules or a surface.

39. A computer usable medium for determining a probability that a biological molecule identification is incorrect for a chosen significance level and for a particular experimental condition, the computer usable medium comprising:

a) a means for generating theoretical mass data for biological molecules;

b) a means for generating experimental mass data for an unknown biological molecule;

c) a means for comparing the experimental mass data generated in step (b) with each theoretical mass data generated in step (a);

d) a means for calculating a score for each comparison in step (c), wherein the score is a function of the similarity between each of the data generated in step (a) and the data generated in step (b);

e) a means for selecting at least two scores from the scores in step (d) to form a primary data set, wherein the scores correspond to a comparison that denotes a degree of similarity between each of the data generated in step (a) and the data generated in step (b);

f) a means for generating a sufficient quantity of artificial data sets from the primary data set in step (e);

g) a means for calculating a sample mean for each artificial data set in step (f);

h) a means for using the sample means generated in step (g) to estimate population mean and population standard deviation; wherein the population is based on the distribution underlying the primary data set;

i) a means for computing a Z score from the population mean and population standard deviation for each score calculated in step (d) to standardize the scores;

j) a means for choosing a significance level; and k) a means for comparing a test Z score to the Z score of the chosen significance level to determine the probability that the identification is incorrect.

40. A computer program product comprising:

a computer usable medium having computer readable program code means embodied in said medium for determining a probability that a biological identification is incorrect for a chosen significance level and for a particular experimental condition, said computer program product including:

computer readable program code means for causing a computer to generate theoretical mass data for known biological molecules, the biological molecules having been cleaved into constituent parts by a method that produces constituent parts;

computer readable program code means for causing a computer to generate experimental mass data for an unknown biological molecule, the unknown biological molecule having been cleaved into constituent parts by a method that produces constituent parts;

computer readable program code means for causing the computer to compare the mass data of the unknown biological molecule with mass data generated for the experimental condition for known biological molecules;

computer readable program code means for causing the computer to calculate scores for each mass data comparison, wherein the scores are a function of similarity between mass data of the unknown biological molecule and mass data generated from the biological molecule database;

computer readable program code means for causing the computer to select at least two scores from the calculated scores to form a primary data set, wherein the selected scores corresponds to a comparison which denotes a high degree of similarity;

computer readable program code means for causing the computer to generate a sufficient quantity of artificial data sets from the primary data set;

computer readable program code means for causing the computer to calculate a sample mean for each artificial data set;

computer readable program code means for causing the computer to estimate population mean and standard deviation; wherein the population is based on the distribution underlying the primary data set;

computer readable program code means for causing the computer to calculate a Z score from the population mean and population standard deviation for each score;

computer readable program code means for causing the computer to choose a significance level;

computer readable program code means for causing the computer to compare a test Z score to a Z score of the chosen significance level to determine the probability that the identification is incorrect.

* * * * *